(12) United States Patent
D' Angelico et al.

(10) Patent No.: US 8,756,980 B2
(45) Date of Patent: Jun. 24, 2014

(54) METHOD FOR DETERMINING AND/OR MONITORING VISCOSITY AND CORRESPONDING APPARATUS

(75) Inventors: Sascha D' Angelico, Efringen-Kirchen (DE); Martin Urban, Zell i. W. (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 511 days.

(21) Appl. No.: 12/733,685

(22) PCT Filed: Aug. 11, 2008

(86) PCT No.: PCT/EP2008/060500
§ 371 (c)(1),
(2), (4) Date: Mar. 15, 2010

(87) PCT Pub. No.: WO2009/037050
PCT Pub. Date: Mar. 26, 2009

(65) Prior Publication Data
US 2010/0236323 A1  Sep. 23, 2010

(30) Foreign Application Priority Data
Sep. 13, 2007  (DE) .......................... 10 2007 043 811

(51) Int. Cl.
*G01N 11/16*  (2006.01)
(52) U.S. Cl.
USPC ....................................................... 73/54.41
(58) Field of Classification Search
USPC ....................................................... 73/54.41
See application file for complete search history.

(56) References Cited

U.S. PATENT DOCUMENTS

| | | | | |
|---|---|---|---|---|
| 3,181,348 A | * | 5/1965 | Lewis ........................... | 73/54.25 |
| 4,023,400 A | * | 5/1977 | November .................... | 73/32 A |
| 5,837,885 A | * | 11/1998 | Goodbread et al. .......... | 73/32 A |
| 6,711,942 B2 | * | 3/2004 | Getman et al. ............... | 73/54.25 |

FOREIGN PATENT DOCUMENTS

| | | |
|---|---|---|
| CN | 1675523 A | 9/2005 |
| DE | 100 50 299 A1 | 4/2002 |
| DE | 102 37 931 A1 | 2/2004 |
| DE | 10 2004 049 580 A1 | 4/2006 |
| DE | 10 2005 020 862 A1 | 11/2006 |
| DE | 10 2005 043 036 A1 | 3/2007 |
| DE | 10 2006 007 199 A1 | 8/2007 |
| EP | 1 361 428 A2 | 11/2003 |
| WO | WO 01/61312 A1 | 8/2001 |

OTHER PUBLICATIONS

Bergaud, Christian and Nicu, Liviu. Viscosity measurements based on experimental investigations of composite cantilever beam eigenfrequencies in viscous media. Rev. Sci. Instrum. 71, 2487 (2000).*

* cited by examiner

*Primary Examiner* — Hezron E Williams
*Assistant Examiner* — Mark A. Shabman
(74) *Attorney, Agent, or Firm* — Bacon & Thomas, PLLC

(57) ABSTRACT

A method for determining and/or monitoring the viscosity of a medium, wherein a mechanically oscillatable unit is excited to execute oscillations based on an exciter signal, and wherein oscillations are received from the mechanically oscillatable unit and transduced into a received signal. The eigenfrequency and/or resonance frequency of the mechanically oscillatable unit and/or phase relationship between the exciter signal and the received signal are/is ascertained and/or monitored, and, from changes in the eigenfrequency and/or resonance frequency and/or phase relationship, a change in viscosity is deduced and/or, based on dependencies of the oscillations on the viscosity of the medium, from the eigenfrequency and/or resonance frequency and/or phase relationship, viscosity is ascertained. In a second variant of the method, decay behavior of the mechanically oscillatable unit is evaluated. An apparatus for determining and/or monitoring viscosity is also presented.

13 Claims, 9 Drawing Sheets

Dynamic Viscosity

Dynamic Viscosity

Dynamic Viscosity

METHOD FOR DETERMINING AND/OR MONITORING VISCOSITY AND CORRESPONDING APPARATUS

TECHNICAL FIELD

The invention relates to a method for determining and/or monitoring at least viscosity of a medium. Other variables to be ascertained, or monitored, include, for example, fill level or density of the medium, wherein the medium involves, for example, a liquid. Furthermore, the invention relates to a corresponding apparatus for determining and/or monitoring at least viscosity of a medium. Other process variables, such as e.g. fill level, are likewise measurable with this apparatus.

BACKGROUND DISCUSSION

In the state of the art, it is known to determine viscosity of a medium with the assistance of a mechanically oscillatable unit (see e.g. DE 100 50 299).

SUMMARY OF THE INVENTION

An object of the invention is to provide other methods with which to determine, or monitor, viscosity of a medium with a mechanically oscillatable unit. Another object is to provide an apparatus for viscosity measurement, or monitoring, which permits measurement, which is as exact as possible.

These objects are achieved according to the invention in a first variant by a method for determining and/or monitoring at least viscosity of a medium, wherein at least one mechanically oscillatable unit is excited to execute mechanical oscillations based on an exciter signal, and wherein mechanical oscillations are received from the mechanically oscillatable unit and transduced into a received signal, wherein eigenfrequency ($\omega_o$) of the mechanically oscillatable unit and/or resonance frequency ($\omega_{res}$) of the mechanically oscillatable unit and/or phase relationship between the exciter signal and the received signal is/are ascertained and/or monitored, and wherein, from changes in the eigenfrequency ($\omega_0$) and/or from changes in the resonance frequency ($\omega_{res}$) and/or from changes in the phase relationship between the exciter signal and the received signal, a change in viscosity is deduced and/or wherein, based on correspondingly furnished dependencies of the oscillations of the mechanically oscillatable unit on viscosity of the medium, viscosity is ascertained from the eigenfrequency ($\omega_0$) and/or resonance frequency ($\omega_{res}$) and/or phase relationship between the exciter signal and the received signal.

The first variant of the method provides, thus, that, from the oscillations of the mechanically oscillatable unit, at least one characteristic variable is ascertained and/or monitored. The characteristic variables are, here, especially, the eigenfrequency ($\omega_0$), the resonance frequency ($\omega_{res}$) and/or the phase relationship between the exciter signal and the received signal. These variables are ascertained and evaluated either individually or in combination as regards viscosity. In such case, a change in the characteristic variables is taken into consideration, in order to detect a change in viscosity, or, starting with the variables, and based on furnished, or stored, relationships (characteristic curves, formulas, algorithms, value pairs, etc.) between the variables and viscosity, viscosity is ascertained.

An embodiment of the first variant of the method of the invention provides that disturbance variables, which, supplementally to viscosity of the medium, influence at least one characteristic variable of the mechanical oscillations of the mechanically oscillatable unit, are essentially kept constant. The oscillations depend not only on viscosity, but, instead, also on the degree of covering of the mechanically oscillatable unit or on the density of the medium. These disturbance variables are, here, kept constant, so that the evaluated variables depend essentially only on viscosity. I.e., the process variables, which can usually be measured, or monitored, with the mechanically oscillatable unit, are, here, in determining viscosity, disturbance variables. The disturbance variable, degree of covering, can, for example, be kept constant by measuring when the mechanically oscillatable unit is completely covered. The density can be essentially kept constant by keeping the temperature constant. Furthermore, the influence of density on the oscillations can be reduced or eliminated by a corresponding optimizing of the geometry of the mechanically oscillatable unit. In this way, also the effects of changes of density on the oscillations are negligible, or no longer present. Thus, an embodiment provides that such a mechanically oscillatable unit is used, and, respectively, optimized, in such a manner with reference to these parameters that the disturbance variables have no, or only negligible, influence on the characteristic variables of the oscillations used for determining viscosity. In practice, for example, an initializing measurement is performed with known disturbance variables, i.e. with known density and known degree of covering, and in subsequent measurements during operation, viscosity is ascertained based on this initializing measurement.

An embodiment of the first variant of the method of the invention includes, that disturbance variables, which, supplementally to viscosity of the medium, influence at least one characteristic variable of the mechanical oscillations of the mechanically oscillatable unit, are ascertained, and that the effect of the disturbance variable and/or a change of the disturbance variable on at least one characteristic variable is taken into consideration in determining and/or monitoring viscosity of the medium. In this embodiment, thus, the dependence of the characteristic variable or the characteristic variables on viscosity and on at least one disturbance variable is known, so that, on the basis of the measuring, or monitoring, of the disturbance variable, viscosity is ascertainable.

An embodiment of the first variant of the method of the invention provides that the degree of covering of the mechanically oscillatable unit by the medium is ascertained and/or monitored. The degree of covering is, thus, one of the disturbance variables.

An embodiment of the first variant of the method of the invention includes that the density of the medium is ascertained and/or monitored. Here, density is a disturbance variable, so it is followed.

An embodiment of the first variant of the method of the invention provides that, starting from the degree of covering of the mechanically oscillatable unit and based on the density of the medium, from changes in the eigenfrequency ($\omega_0$) and/or from changes in the resonance frequency ($\omega_{res}$) and/or from changes in the phase relationship between the exciter signal and the received signal, a change in viscosity is deduced. If the disturbance variables are essentially constant and a characteristic variable is considered, which is dependent on viscosity, then, from the change of the characteristic variable, the change in viscosity can be deduced.

An embodiment of the first variant of the method of the invention includes that, starting from the degree of covering of the mechanically oscillatable unit and based on the density of the medium, and based on correspondingly furnished dependencies of the oscillations of the mechanically oscillatable unit on viscosity of the medium, from the eigenfrequency ($\omega_0$) and/or resonance frequency ($\omega_{res}$) and/or phase relationship between the exciter signal and the received signal, viscosity is ascertained. The disturbance variables, density and fill level, are, here, either essentially kept constant or the dependence of characteristic variables on these is known and is suitably taken into consideration in determining viscosity based on furnished dependencies between characteristic variable, or characteristic variables, of the oscillations and viscosity.

An embodiment of the first variant of the method of the invention provides that a mechanically oscillatable unit is used, whose oscillations are essentially independent of the density of the medium.

An embodiment of the first variant of the method of the invention includes that the eigenfrequency ($\omega_0$) of the mechanically oscillatable unit is ascertained, and that viscosity of the medium is ascertained based on at least one furnished relationship between eigenfrequency ($\omega_0$) and viscosity.

An embodiment of the first variant of the method of the invention provides that the resonance frequency ($\omega_{res}$) of the mechanically oscillatable unit is ascertained, and that viscosity of the medium is ascertained based on at least one furnished relationship between the resonance frequency ($\omega_{res}$) and viscosity.

An embodiment of the first variant of the method of the invention includes that the phase difference between the exciter signal and the received signal is ascertained for oscillations of the mechanically oscillatable unit at the resonance frequency ($\omega_{res}$), and that viscosity of the medium is ascertained based on at least one furnished relationship between phase difference and viscosity.

An embodiment of the first variant of the method of the invention provides that at least one relationship between eigenfrequency ($\omega_0$) and resonance frequency ($\omega_{res}$) of the mechanically oscillatable unit is ascertained, and that viscosity of the medium is ascertained based on at least one furnished relationship between the relationship and viscosity.

An embodiment of the first variant of the method of the invention includes that a quotient of eigenfrequency ($\omega_0$) and resonance frequency ($\omega_{res}$) of the mechanically oscillatable unit is formed, and that viscosity of the medium is ascertained based on at least one furnished relationship between the quotient and viscosity.

The invention solves the objects in a second variant by a method for determining and/or monitoring at least viscosity of a medium, wherein at least one mechanically oscillatable unit is excited to execute mechanical oscillations based on an exciter signal, and wherein mechanical oscillations are received from the mechanically oscillatable unit and transduced into a received signal, wherein, after the exciting of oscillations of the mechanically oscillatable unit, decay of the oscillations of the mechanically oscillatable unit is ascertained, and wherein, from changes in the decay, a change in viscosity is deduced, and/or wherein, based on correspondingly furnished dependencies of the decay of the oscillations of the mechanically oscillatable unit on viscosity of the medium, viscosity is ascertained from the ascertained decay.

Common to the two variants of the invention is that each references the oscillatory behavior of the mechanically oscillatable unit and its dependence on viscosity of the medium for determining, or monitoring, viscosity of the medium. In the case of the first variant, the mechanically oscillatable unit is lastingly excited to execute oscillations, and, in the case of the second variant, there is an exciting, which is limited in time and, preferably, periodically recurring.

The above discussed embodiments as regards monitoring, or measuring and processing, the disturbance variables hold correspondingly also for the second variant.

Furthermore, the invention relates to an apparatus for determining and/or monitoring at least viscosity of a medium. The apparatus includes: At least one mechanically oscillatable unit; and at least one evaluation unit, which supplies the mechanically oscillatable unit with an exciter signal and receives from the mechanically oscillatable unit a received signal. The apparatus is characterized in that the mechanically oscillatable unit is embodied in such a manner, that the mechanical oscillations of the mechanically oscillatable unit are essentially independent of density and/or a change of density of the medium. The oscillations of the mechanically oscillatable unit are, thus, essentially independent of density of the medium, so that this disturbance variable has essentially no effect in the determining, or monitoring, of viscosity. The mechanically oscillatable unit is, thus, flow optimized, or optimized for viscosity measurement, or for preventing effects of density.

An embodiment of the apparatus of the invention provides that the mechanically oscillatable unit includes at least one membrane, or diaphragm, and two fork tines, wherein the fork tines are embodied essentially cylindrically.

Thus, mounted on a membrane, or diaphragm, are at least two cylinders or tubes. The cross section of the fork tines is, in such case, circular, oval or elliptical.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 1:
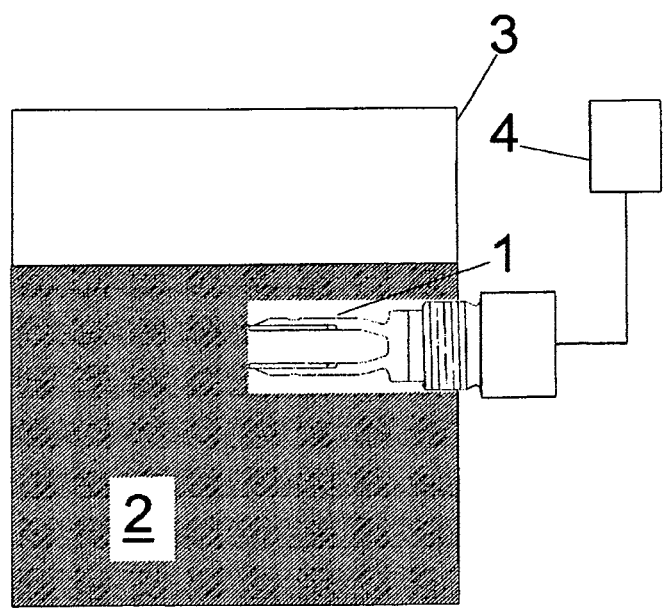
FIG. 1 is a schematic representation of measuring with an oscillatory fork.

FIG. 1 shows the measuring method, in principle, with a mechanically oscillatable unit 1. The mechanically oscillatable unit 1 is, in this example, a so-called oscillatory fork. Alternative embodiments include membrane, or diaphragm, oscillators, or so-called single rods. In the case of the here illustrated, oscillatory fork, the mechanically oscillatable unit 1 is composed of two fork tines, which are secured on a membrane, or diaphragm.

On the inside of the membrane, or diaphragm, is located a driving/receiving unit (not shown), in the form, for example, of a piezoelectric element. The driving/receiving unit transduces, for example, an electrical alternating voltage as exciter signal into mechanical movements of the membrane, or diaphragm, and, thereby, the fork tines and, thus, the mechanically oscillatable unit 1 as a whole. Conversely, the driving/receiving unit serves also for transducing the mechanical oscillations of the mechanically oscillatable unit into an electrical signal, which is, here, likewise, an electrical, alternating voltage. This is the received signal.

The mechanically oscillatable unit 1 is placed on the wall of the container 3 in such a manner, that it comes in contact with the medium 2 at a certain fill level thereof, or in such a manner that the mechanically oscillatable unit 1 is covered to a certain degree by the medium 2 at a desired fill level of the medium 2. In an embodiment, the mechanically oscillatable unit 1 is completely covered by the medium 2. Medium 2 is, in such case, especially, a liquid.

From the characteristic variables of the oscillations of the mechanically oscillatable unit 1, such as special frequencies, amplitude or phase relationship of the received signal relative to the exciter signal, in given cases, as a function of the particular frequency, process variables of the medium 2 can be determined, or changes of these process variables monitored.

Thus, for example, fill level can be monitored by the fact that the frequency, or the amplitude, is reduced, when the mechanically oscillatable unit 1 comes in direct contact with the medium 2, or, conversely, from an increasing of the amplitude, or the frequency, it can be deduced, that the medium 2 has a fill level below the mechanically oscillatable unit 1.

For determining, or monitoring, such process variables, for instance viscosity, or density, of the medium 2, in most cases, a certain fill level of the medium 2, i.e. a certain degree of covering of the mechanically oscillatable unit 1 by the medium 2, is chosen.

The driving of the mechanically oscillatable unit and, respectively, the evaluation the measuring signals is performed here by an evaluation unit 4. Furnished, e.g. stored, in this evaluation unit 4 are the dependencies of the variables of the oscillations of the mechanically oscillatable unit to be measured, or to be monitored, on viscosity. These dependencies can be stored, for example, in the form of tables, selected value pairs (hash tables) or in the form of functional relationships.

Since density and fill level, or degree of covering, are disturbance variables in determining, or monitoring, viscosity, these are kept constant, for example, by the boundary conditions of the measuring or, for example, a measuring, or monitoring, of the disturbance variables is performed by additional measuring devices. In an alternative embodiment, the density of the medium is measured by the same mechanically oscillatable unit as for used viscosity, by tuning a phase between the excitation signal and the received signal set, at which the oscillations are essentially independent of viscosity, or a change in viscosity. I.e., density and viscosity are measured with one measuring device. When the disturbance variables are held constant, knowledge of the dependence of a characteristic variable, or a number of characteristic variables, of the oscillations on viscosity of the medium is sufficient, in order to make statements concerning viscosity. If the disturbance variables change and the disturbance variables are measured, then knowledge concerning this, thus, multidimensional dependence is required, or the data must be suitably furnished, or stored in the evaluation unit 4.

Figure 2:
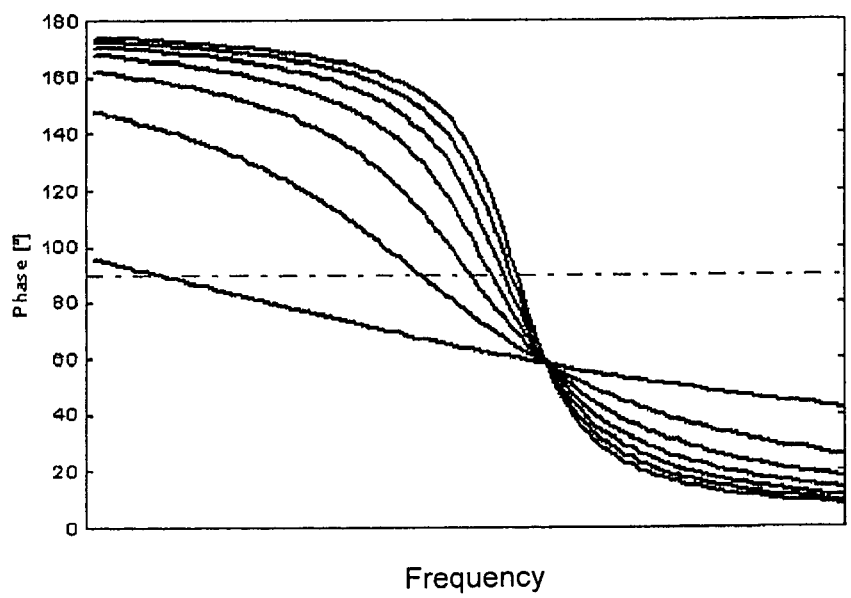
FIG. 2 shows dependence of eigenfrequency on viscosity of the medium in the case of constant density of the medium.

FIG. 2 shows the viscosity dependent behavior of the eigenfrequency $\omega_0$ of the oscillations of the mechanically oscillatable unit. Represented is the dependence of phase of the oscillations of the received signal relative to the exciter signal as a function of the frequency of the oscillations in the case of known, or fixed, density of the medium. The eigenfrequency $\omega_0$ is, in such case, characterized in that it is the oscillation frequency, at which the phase of the oscillations and, thus, the received signal, relative to the exciter signal is 90°. This phase of 90° is shown in the figure by the horizontal, dot dashed line. I.e., from the intersection of the line with the curve, there results the eigenfrequency $\omega_0$ present in the case of the particular viscosity of the medium. The individual curves belong in such case to media with equal density, however, different viscosity.

As clearly recognizable, as a function of viscosity, in each case, a clearly different eigenfrequency $\omega_0$ is present. Thus, it is possible, based on the eigenfrequency $\omega_0$, at known density, to deduce viscosity. In the case, wherein only a change in viscosity should be detected, it is already sufficient to detect a change of eigenfrequency $\omega_0$ in the case of unchanged density, or unchanged degree of covering, or process conditions otherwise generally kept constant.

The eigenfrequency $\omega_0$ is in such case ascertained in such a manner, that a frequency range is run through and the phases are evaluated. The frequency, at which a phase difference of 90° occurs, is, thus, the eigenfrequency $\omega_0$. Another opportunity is to set a phase difference of 90° and to measure the resulting frequency. This is then the eigenfrequency $\omega_0$.

FIG. 3 details again the dependence of change of eigenfrequency $\omega_0$ on the dynamic viscosity of the medium. The dynamic viscosity describes in such case the viscous behavior of the medium without taking into consideration the density of the medium. Taking density into consideration yields the kinematic viscosity.

Figure 3:
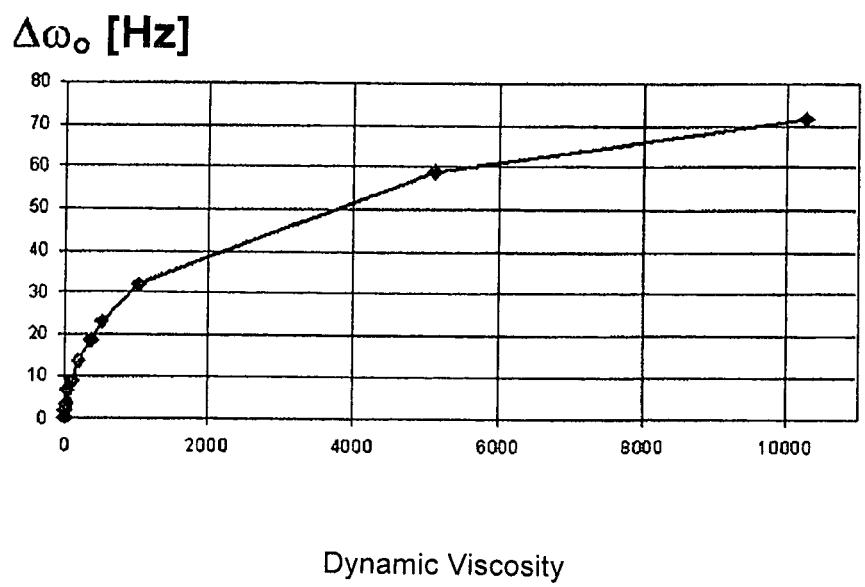
FIG. 3 shows dependence of change of eigenfrequency on viscosity of the medium in the case of constant density of the medium.

The frequencies of FIG. 3 are given in such case relative to the eigenfrequency of a mechanically oscillatable unit, for example, as illustrated in FIG. 1 in the case of oscillations in water (density=1 and viscosity=1).

The eigenfrequency $\omega_0$ and resonance frequency $\omega_{res}$ of the oscillations of the mechanically oscillatable unit are related to one another as a function of the damping D: $\omega_{res}=\omega_0 \cdot \sqrt{1-2\cdot D^2}$.

In the case of resonance frequency $\omega_{res}$, such is that frequency, at which the amplitude of the oscillations has its local maximum. In the case, that no damping is present, or that the damping is negligible, then the resonance frequency (ores and the eigenfrequency $\omega_0$ are the same.

If one considers an almost density insensitive oscillatory system (compare FIG. 5), then the eigenfrequency $\omega_0$ can be assumed to be constant and then alone the damping effect of viscosity on the oscillatory system of the mechanically oscillatable unit is measured by the evaluation of frequency.

Figure 4:
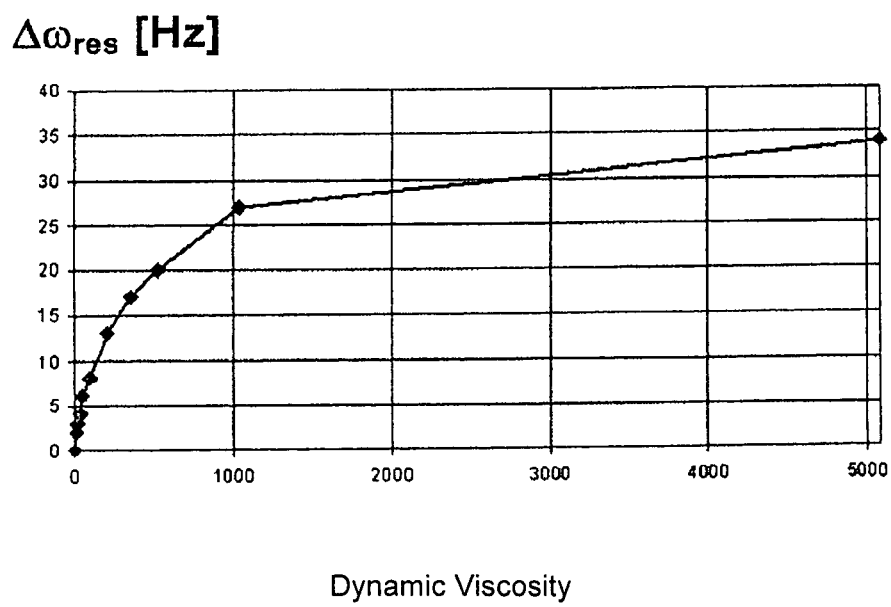
FIG. 4 shows dependence of change of resonance frequency on viscosity of the medium in the case of constant density of the medium.

FIG. 4 shows the dependence of change of resonance frequency $\omega_{res}$ on the dynamic viscosity $\eta$ in the case of constant density $\rho$ of the medium. The resonance frequency $\omega_{res}$ is in such case measured in such a manner, that a certain frequency band is run through, and the amplitude evaluated. Thus, also the resonance frequency $\omega_{res}$ permits monitoring, or in the case of suitably furnished values, or dependencies, the ascertaining of viscosity.

Figure 5:
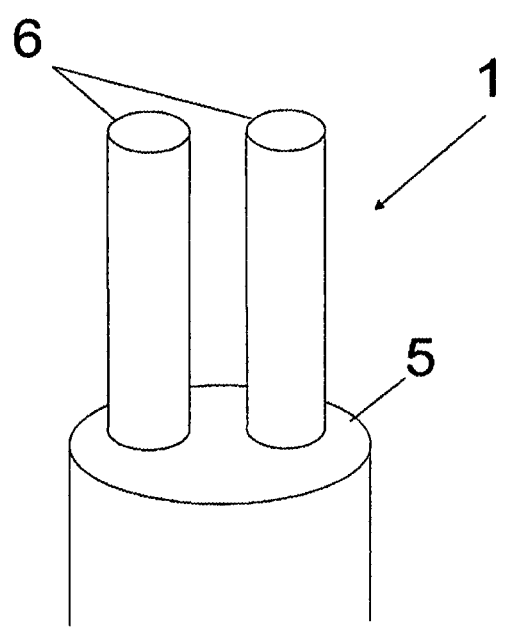
FIG. 5 is a schematic representation of a variant of the mechanically oscillatable unit.

FIG. 5 shows another embodiment of the mechanically oscillatable unit 1, in the case of which the two fork tines are round rods. Advantageous with these round rods is that the oscillations are almost independent of the density of the medium. In the case that, in determining, or monitoring, viscosity, a geometry of the mechanically oscillatable unit 1 is used, which leads to the fact that this unit 1, or its oscillations, are density dependent, either it must be assumed, that the density remains constant within a certain range, or the dependence of oscillations on density must be previously known. The membrane, or diaphragm, is, here, circular and also the fork tines have a circularly shaped cross section.

Since the resonance frequency $\omega_{res}$ and the eigenfrequency $\omega_0$ of the oscillatory system differ from one another in the case, in which the influences of viscosity and density are not negligible, it will become evident in the case of resonance frequency $\omega_{res}$ that phase relationships between the exciter signal and the received signal do not equal 90°. It can be observed, that the phase difference in the case of resonance frequency $\omega_{res}$ sinks with increasing viscosity. This dependence, or this relationship, permits, thus, also a determining, or monitoring, of viscosity. Density is, in such case, a disturbance variable.

Figure 6:
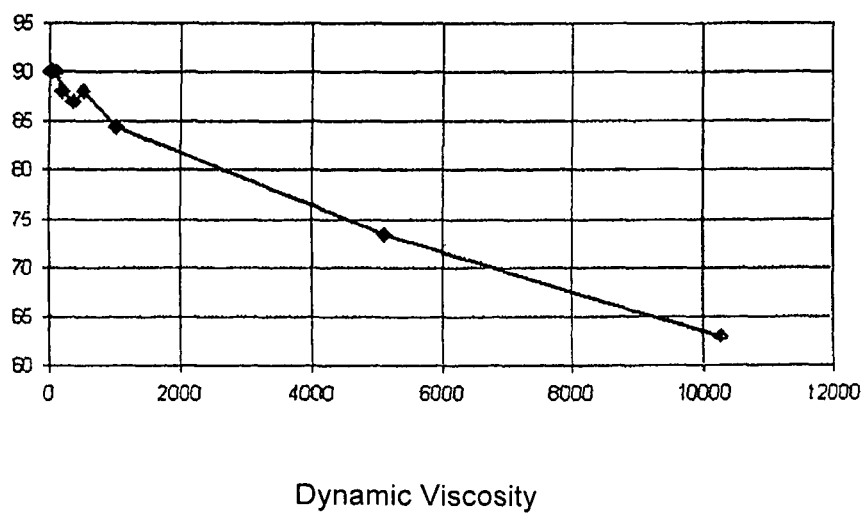
FIG. 6 shows dependence of phase of received signal relative to exciter signal at resonance frequency on viscosity of the medium in the case of constant density of the medium.

FIG. 6 shows such a relationship between the phase angle in the case of resonance frequency $\omega_{res}$ and the dynamic viscosity of the medium. Shown is that, in the case of a viscosity of the medium of zero, the phase angle amounts to 90°. If, thus, in the case of known or constant density and in the case of known or constant degree of covering, with oscillations of the mechanically oscillatable unit at the resonance frequency $\omega_{res}$, the phase between the received signal and the exciter signal is ascertained, then, therefrom, a change in viscosity, or even the measure of viscosity itself, can be deduced.

Figure 7:
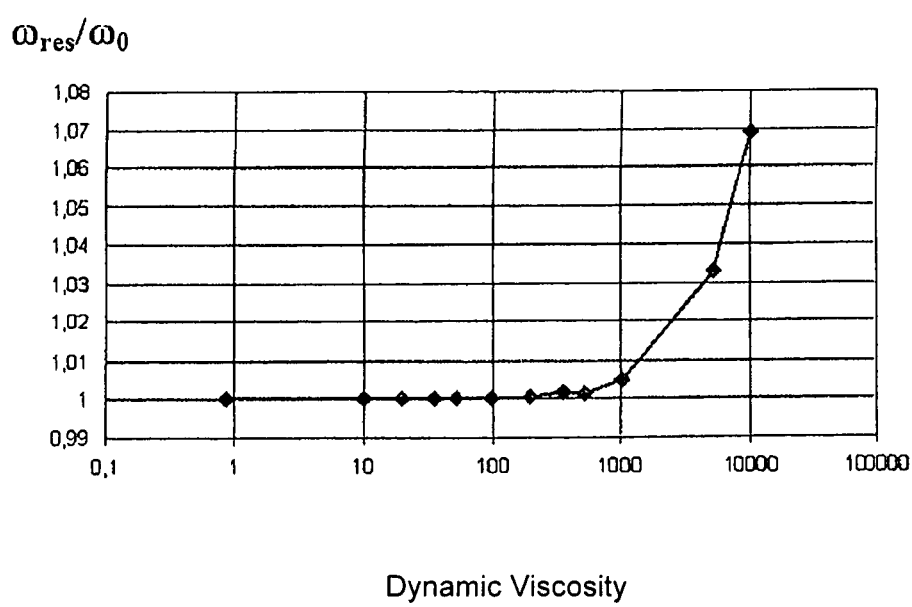
FIG. 7 shows dependence of quotient of resonance frequency and eigenfrequency on viscosity of the medium.

FIG. 7 shows the ratio between resonance frequency, $\omega_{res}$, and eigenfrequency, $\omega_0$, of the mechanically oscillatable unit as a function of viscosity. If both the resonance frequency $\omega_{res}$ as well as also the eigenfrequency $\omega_0$ of the mechanically oscillatable unit is ascertained, then these two measured values can be divided one by the other to form their ratio. As FIG. 7 indicates, also evaluation of this quotient permits monitoring, or determining, of viscosity of the medium.

The methods described in the preceding figures for determining, or monitoring, viscosity assume, in each case, that at least one frequency of the mechanically oscillatable unit, or, generally, the oscillatory system, is ascertained, or monitored, and that the viscosity dependence of the particular frequency, or, associated therewith, the phase, is used. In the following figures, a further method is presented, namely the second variant, in the case of which the dependence of the oscillatory behavior of the oscillatory system on viscosity in another way is utilized. In the previous methods, it is assumed, that the oscillatory system is excited continually to execute oscillations and that, thus, continuously, oscillation parameters are evaluated.

Figure 8:
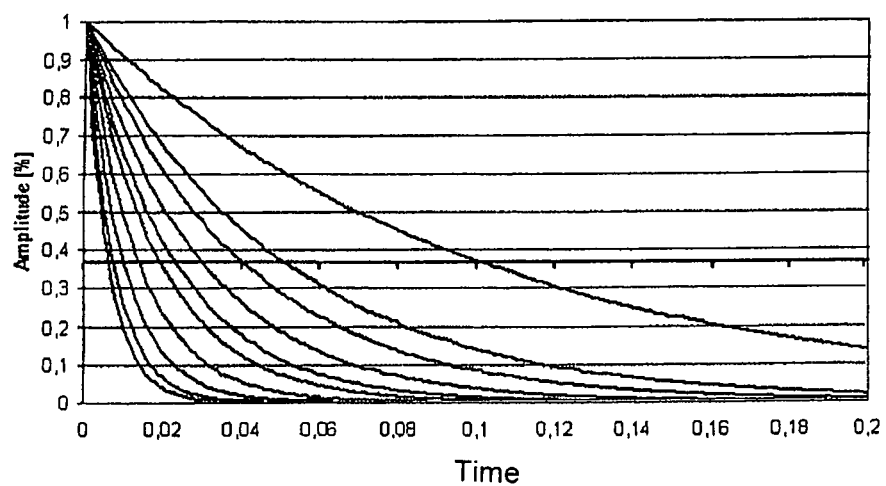
FIG. 8 shows dependence of amplitude in the case of the decay behavior of the mechanically oscillatable unit in the case of constant density of the medium.

FIG. 8 shows the decay behavior of the mechanically oscillatable unit in various media. The oscillatable unit is, in such case, excited to execute oscillations and the decrease of the amplitude after the one-time exciting is plotted versus time and evaluated. As can be seen, the curves are functionally dependent on the viscosity of the medium. In such case, it is to be observed that, with increasing viscosity, i.e. with increasing damping, the decay is faster, so that, in a high viscosity medium, the oscillations go faster to zero than in a low viscosity medium. Alternatively to the decay of the oscillatory system, also transient response can be evaluated.

For ascertaining the decay, or the transient response, of the oscillatory system, the system should preferably be operated in resonance, in order to enable a highest possible amplitude and, thus, a good evaluation. The exciting of the oscillatory system operated in resonance is, in such case, switched off, in order to record, or measure, the decay. This can be described, for example, by a step function: $(1-\sigma(t)) \cdot A \cdot \sin(\omega \cdot t)$.

The decay curves of the amplitudes A(t) can, in such case, be described, for example, by an exponential function of the following form:

$$A(t) = \hat{A} \cdot e^{-\frac{1}{T} \cdot t} = \hat{A} \cdot e^{-\delta \cdot t}.$$

Such curves are shown in FIG. 8, in the case of which, in each case, the density of the medium remains the same. The amplitude is, in each case, given in percentage referenced to the first measured, amplitude value.

For determining the time constant $\delta$, the time is ascertained, at which the amplitude has declined to about 36.8%, corresponding to 1/e. FIG. 8 shows, in such case, this threshold value by a thicker line. It is to be recognized that, with sinking viscosity, the measuring, or determining, of the decay time and, thus, the determining of the decay constant $\delta$, can always occur more exactly, since, on the one hand, higher amplitudes of the oscillations can be expected and since, on the other hand, the decay times are always larger and, thus, are more exactly ascertainable.

As an add-on to the determining of the decay time constant $\delta$, an opportunity is to normalize this constant $\delta$ on the particular eigenfrequency $\omega_0$ of the oscillatory system, in order, in this way, to obtain Lehr's damping ratio. Lehr's damping ratio is defined as follows:

$$\Delta = \frac{\delta}{\omega_0}.$$

Figure 9:
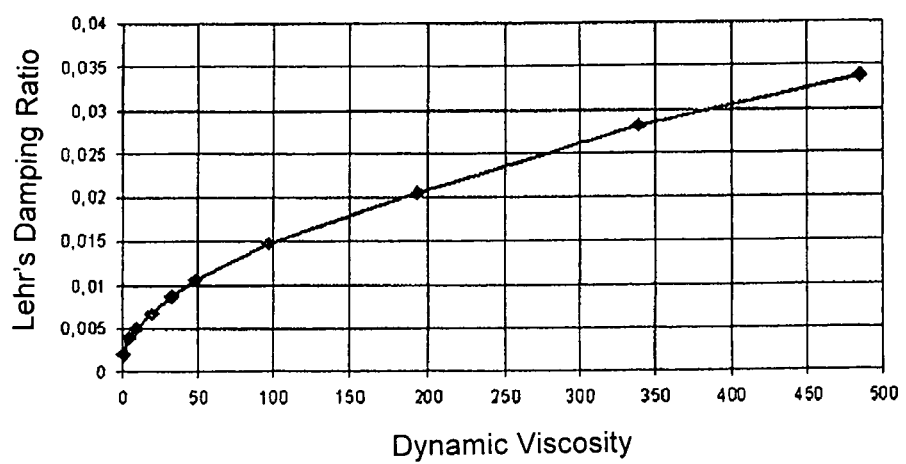
FIG. 9 shows dependence of Lehr's damping ratio on viscosity.

FIG. 9 shows the viscosity dependence of Lehr's damping ratio. In such case, it is clearly recognizable that, based on decay as a function of eigenfrequency $\omega_0$, the determining of viscosity is possible. Thus, ascertained, on the one hand, is the eigenfrequency $\omega_0$, and, on the other hand, the time constant of the decay, and the two variables are taken into consideration for establishing Lehr's damping ratio, wherein the actual, or measured, value permits, via comparison with suitably stored data, the determining of viscosity of the medium.

| List of Reference Characters | |
|---|---|
| 1 | mechanically oscillatable unit |
| 2 | medium |
| 3 | container |
| 4 | evaluation unit |
| 5 | membrane, or diaphragm |
| 6 | fork tines |

The invention claimed is:
1. A method for determining and/or monitoring at least the viscosity of a medium, comprising the steps of:
   exciting at least one mechanically oscillatable unit to execute mechanical oscillations based on an exciter signal;
   receiving mechanical oscillations by the mechanically oscillatable unit and transducing them into a received signal; and
   ascertaining and/or monitoring the eigenfrequency of the mechanically oscillatable unit and/or the phase relationship between the exciter signal and the received signal, wherein:

from changes in the eigenfrequency and/or from changes in the phase relationship between the exciter signal and the received signal, with oscillations of the mechanically osillatable unit at the resonance frequency, a change in viscosity is deduced; and/or based on dependencies of the oscillations of the mechanically oscillatable unit on the viscosity of the medium, from the eigenfrequency and/or phase relationship between the exciter signal and the received signal, with oscillations of the mechanically oscillatable unit at the resonance frequency, viscosity is ascertained.

2. The method as claimed in claim 1, wherein:
disturbance variables, which, supplement to viscosity of the medium, influence at least one characteristic variable of the mechanical oscillations of the mechanically oscillatable unit, are essentially kept constant.

3. The method as claimed in claim 1, wherein:
disturbance variables, which, supplement to viscosity of the medium, influence at least one characteristic variable of the mechanical oscillations of the mechanically oscillatable unit are ascertained, and the effect of the disturbance variable and/or a change of the disturbance variable on at least one characteristic variable is taken into consideration in determining and/or monitoring the viscosity of the medium.

4. The method as claimed in claim 2, wherein:
the degree of covering of the mechanically oscillatable unit by the medium is ascertained and/or monitored.

5. The method as claimed in claim 2, wherein:
the density of the medium is ascertained and/or monitored.

6. The method as claimed in claim 5, wherein:
starting from the degree of covering of the mechanically oscillatable unit and based on the density of the medium, from changes in the eigenfrequency and/or from changes in the phase relationship between the exciter signal and the received signal, a change in viscosity is deduced.

7. The method as claimed in claim 5, wherein:
starting from the degree of covering of the mechanically oscillatable unit and starting from density of the medium, based on the dependencies of the oscillations of the mechanically oscillatable unit on the viscosity of the medium, from the eigenfrequency and/or phase relationship between the exciter signal and the received signal, viscosity is ascertained.

8. The method as claimed in claim 1, wherein:
a mechanically oscillatable unit is applied, whose oscillations are essentially independent of the density of the medium.

9. The method as claimed in claim 1, wherein:
the eigenfrequency of the mechanically oscillatable unit is ascertained, and the viscosity of the medium is ascertained based on at least one relationship between eigenfrequency and viscosity.

10. The method as claimed in claim 1, wherein:
the phase difference between the exciter signal and the received signal is ascertained for oscillations of the mechanically oscillatable unit at the resonance frequency, and the viscosity of the medium is ascertained based on at least one relationship between phase difference and viscosity.

11. The method as claimed in claim 10, wherein:
at least one relationship between eigenfrequency and resonance frequency of the mechanically oscillatable unit is ascertained, and the viscosity of the medium is ascertained based on at least one relationship between the relationship and viscosity.

12. The method as claimed in claim 11, wherein:
a quotient of eigenfrequency and resonance frequency of the mechanically oscillatable unit is formed, and the viscosity of the medium is ascertained based on at least one relationship between the quotient and the viscosity.

13. A method for determining and/or monitoring at least viscosity of a medium, comprising the steps of:
exciting at least one mechanically oscillatable unit with oscillations at the resonance frequency, to execute mechanical oscillations based on an exciter signal;
receiving mechanical oscillations from the mechanically oscillatable unit and transducing them into a received signal; and
ascertaining the decay of the oscillations of the mechanically oscillatable unit after exciting an oscillation of the mechanically oscillatable unit with oscillations at the resonance frequency, wherein:
from changes in the decay, a change in viscosity is deduced; and/or based on dependencies of the decay of the oscillations of the mechanically oscillatable unit on the viscosity of the medium, viscosity is ascertained from the ascertained decay.

* * * * *